US00PP11561P

United States Patent [19]

Zary

[11] Patent Number: Plant 11,561

[45] Date of Patent: Oct. 10, 2000

[54] FLORIBUNDA ROSE PLANT NAMED 'JACEXTRA'

[75] Inventor: Keith W. Zary, Thousand Oaks, Calif.

[73] Assignee: Bear Creek Gardens, Inc., Medford, Oreg.

[21] Appl. No.: 09/234,791

[22] Filed: Jan. 20, 1999

[51] Int. Cl.[7] ..... A01H 5/00

[52] U.S. Cl. ..... Plt./148

[58] Field of Search ..... Plt./148, 149, 141, Plt./144

*Primary Examiner*—Howard J. Locker

*Attorney, Agent, or Firm*—Klarquist Sparkman Campbell Leigh & Whinston, LLP

[57] ABSTRACT

Floribunda rose plant having long stems, high greenhouse cut flower production, flowers presented in clusters, good vase life, and a flower color in the light pink range.

1 Drawing Sheet

The present invention relates to a new and distinct variety of rose plant of the floribunda rose class which was originated by me by crossing the variety 'INTERprince', (U.S. Plant Pat. No. 8,102), with an unnamed seedling.

The primary objective of this breeding was to produce a new rose variety having long stems, high greenhouse cut flower production, flowers presented in clusters, good vase life, and a flower color in the light pink range. The objective was substantially achieved, along with other desirable improvements, as evidenced by the following unique combination of characteristics that are outstanding in the new variety and that distinguish it from its parents, as well as from all other varieties of which I am aware:

1. Flowers presented in clusters of three to seven blooms;
2. Cut flower production of 160–170 stems/$m^2$ of greenhouse;
3. Stems are long and strong, averaging 18–22 inches long;
4. Vase life is good at 11–12 days, and;
5. Flower color is an attractive, very pure pink.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'INTERprince' (U.S. Plant Pat. No. 8,102).

*Pollen parent.*—Unnamed seedling (unnamed seedling×unnamed seedling).

Classification:

*Botanical .*—*Rosa hybrida.*

*Commercial .*—Floribonda.

FLOWER

Observations made from specimens grown in a greenhouse environment at Somis, Calif., January 1996 to December 1998.

Blooming habit: Continuous.

Bud:

*Size.*—One and one-quarter inches long when the petals start to unfurl.

*Form.*—The bud form is long, pointed ovoid.

*Color.*—When sepals first divide, bud color is Red Group 49C. When half blown, the upper sides of the petals are Red Group 49C. On the lower sides of the petals the color is Red Group 49C.

*Sepals.*—Color: Green Group 138B. Surface texture: Covered in fine hairs. There are three lightly appendaged sepals. There are two unappendaged sepals with smooth edges.

*Receptacle.*—Color: Green Group 137D. Shape: Funnel. Size: Small, about ¼"×¼". Surface: Smooth.

*Peduncle.*—Length: Short, averaging about one and one-half inches. Surface: Smooth. Color: Green Group 137D. Strength: Stiff, erect.

Bloom:

*Size.*—Medium. Average open size is three inches.

*Borne.*—Several together in flat clusters of three to seven blooms.

*Stems.*—Strength: Strong. Average length is about eighteen to twenty-two inches.

*Form.*—When first open: High-centered. Permanence:. All petals curl, with some quilling.

*Petalage.*—Number of petals under normal conditions: 25-30.

*Color.*—The upper sides of the petals are Red Group 49C. The reverse sides of the petals are Red Group 49C. The base of each petal has, on both surfaces, a small (⅛"×⅛"), Yellow Group 3C half moon at the point of attachment. The major color on the upper side is Red Group 49C.

*Variegations.*—There are greenish streaks on the upper surface of some guard petals. The streaks follow the midrib and are close to Yellow-Green Group 154C.

*Discoloration.*—The general tonality at the end of the first day: No change. At the end of the third day: No change.

*Fragrance.*—None.

Petals:

*Texture.*—Thick.

*Shape.*—Deltoid.

*Form.*—Tips slightly recurved, edges slightly quilled.

*Arrangement.*—Imbricated. Petaloids in the center: Few to none. If present, they are from one to three. They average about three-quarters inch long and one-quarter inch wide and are Red Group 49C.

*Persistence.*—Petals drop off cleanly before drying.

*Lastingness.*—On the plant: Fair (seven days). As a cut flower: Long (about eleven to twelve days).

Reproductive parts:

*Anthers.*—Size: Medium. Quantity: Many. Color: Yellow-Orange Group 22C. Arrangement: Regular around styles.

*Filaments.*—Color: Green-Yellow Group 1D.

*Pollen.*—Present.

*Styles.*—Color: White Group 155D.

*Stigmas.*—Color: Orange-White Group 159B.

Plant:

*Form.*—Bush.

*Growth.*—Vigorous, upright, branching. Mature plant height is about four and one-half feet, width is about three feet.

Foliage: Number of leaflets on normal mid-stem leaves: Five or seven.

*Size.*—Large (7" long×4½" wide).

*Quantity.*—Abundant.

*Color.*—New foliage: Upper surface: Yellow-Green Group 146B edged in Greyed-Orange Group 176A. Lower surface: Greyed-Orange Group 176A. Old foliage: Upper surface: Green Group 139A. Lower surface: Green Group 138B.

Leaflets:

*Shape.*—Pointed oval.

*Texture.*—Leathery.

*Edge.*—Serrated.

*Serration.*—Single, small.

*Petiole rachis.*—Green Group 138B.

*Petiole underside.*—Rough with prickles.

*Stipules.*—Long (¾"), serrated, bearded.

*Disease resistance.*—Resistant to mildew under normal growing conditions in a greenhouse. Not tested for blackspot and rust.

Wood:

*New wood.*—Color: Green Group 137D. Bark: Smooth.

*Old wood.*—Color: Green Group 137C. Bark: Smooth.

Prickles:

*Quantity.*—On main canes from base: Ordinary. On laterals from main canes: Ordinary.

*Form.*—Medium, hooked slightly downward.

*Color when young.*—Greyed-Orange Group 176C.

*Color when mature.*—Greyed-Orange Group 173D.

Small prickles:

*Quantity.*—On main stalks: None. On laterals: None.

I claim:

1. A new and distinct variety of rose plant of the floribunda class, substantially as herein shown and described, characterized particularly by long stems, high greenhouse cut flower production, flowers presented in clusters, good vase life, and a flower color in the light pink range.

* * * * *

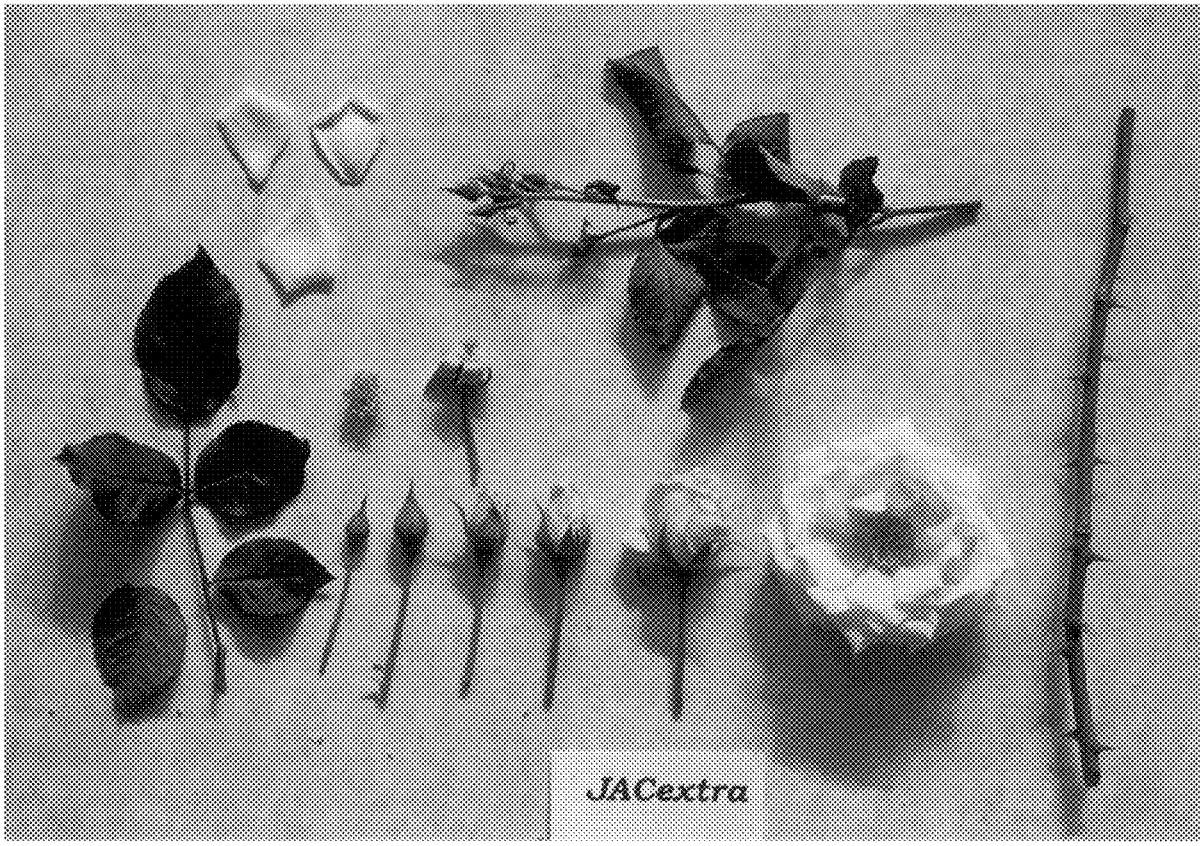
JACextra